United States Patent [19]

Juenger

[11] Patent Number: 4,586,523
[45] Date of Patent: May 6, 1986

[54] CLEANING CONTROL THROUGH MEASUREMENT OF ELECTRICAL CONDUCTIVITY

[75] Inventor: Rudolf Juenger, Kreuzau, Fed. Rep. of Germany

[73] Assignee: Akzona Incorporated, Asheville, N.C.

[21] Appl. No.: 697,407

[22] Filed: Feb. 1, 1985

Related U.S. Application Data

[62] Division of Ser. No. 506,496, Jun. 21, 1983, Pat. No. 4,515,641.

[30] Foreign Application Priority Data

Jun. 28, 1982 [DE] Fed. Rep. of Germany ....... 3224016

[51] Int. Cl.⁴ .......................... B08B 9/08; B08B 13/00
[52] U.S. Cl. .................................................... 134/113
[58] Field of Search ................. 134/5, 18, 22.1, 22.11, 134/113; 324/65 R; 68/12 R

[56] References Cited

U.S. PATENT DOCUMENTS

| | | |
|---|---|---|
| 2,183,584 | 12/1939 | Pedersen . |
| 2,662,041 | 12/1953 | Dougherty et al. ..................... 134/5 |
| 2,697,673 | 12/1954 | Rice .................................. 134/18 X |
| 2,909,483 | 10/1959 | Williams et al. . |
| 3,540,868 | 11/1970 | Chevion et al. .............. 324/65 R X |
| 3,864,083 | 2/1975 | Green ........................... 324/65 R X |
| 3,910,997 | 10/1975 | Andersen et al. .................. 134/5 X |
| 3,973,572 | 8/1976 | Brous ............................... 134/113 X |
| 4,068,162 | 1/1978 | Robinson . |
| 4,280,852 | 7/1981 | Dunham et al. .................. 134/18 X |
| 4,375,991 | 3/1983 | Sachs et al. ........................ 134/18 X |
| 4,415,859 | 11/1983 | Slough et al. ................. 324/65 R X |

FOREIGN PATENT DOCUMENTS 2542141 3/1977 Fed. Rep. of Germany ...... 134/113

Primary Examiner—Philip R. Coe
Attorney, Agent, or Firm—Parkhurst & Oliff

[57] ABSTRACT

There is disclosed a process for cleaning the interior wall of a metal vessel or pipe comprising flooding or turbulently impacting the interior wall of said vessel or pipe with a strongly alkaline or strongly acidic cleaning fluid, simultaneously measuring the conductivity of the cleaning fluid between two electrodes located in the interior of said vessel or pipe and terminating said flooding or impacting when the measured conductivity has been substantially restored to the level measurable with clean electrodes. There is also disclosed an apparatus for performing the process.

17 Claims, 2 Drawing Figures

CLEANING CONTROL THROUGH MEASUREMENT OF ELECTRICAL CONDUCTIVITY

This is a Divisional application of Ser. No. 506,496 filed June 21, 1983 now U.S. Pat. No. 4,515,641.

BACKGROUND OF THE INVENTION

The present invention concerns a process and an apparatus for the control of the degree of cleanliness of metallic surfaces of containers, equipment, or pipelines. The invention is especially of interest in areas in which the cleanliness is to be checked at inaccessible, or not visible locations, such as the interior walls of containers, equipment, or pipes of that kind.

Because of the impossibility of a visual inspection, or the bother of checking such interior surfaces, control measures are often even omitted entirely in practice. In those cases, cleanliness is simply assumed on the basis of the experience that, in general, after cleaning measures under defined conditions, the container, equipment, or pipe should to be clean. In those cases in which one did not want to do without a cleanliness control, the following measures have been taken:

- Investigation of the washing liquid after emerging from the equipment to be cleaned; this liquid is evaluated either visually, or by exact analytical methods.
- Determination of the contamination by back-weighing ("Seifen, Fette, Oele, Wachse" 1953, pp. 488–489, 514–516, 540–542, 568–569, 597–599, 622–625, 645–647).
- Recording of the radioactive residual radiation of the contamination mixed with tracer substance ("Fette, Seifen, Anstrichmittel" 80 (1978), pp. 43–50, 80–85, 118–124).

The disadvantages of the foregoing measures are obvious: either the degree of cleanliness can only be roughly estimated or cannot be determined in the region of small quantities due to the limits of analytical measuring methods. In addition, these measures are cumbersome, time consuming, or even hazardous (the latter e.g. in the case of radioactive recording). Cumbersome and time-consuming are e.g. those cleaning processes where absolute cleanliness of the interior walls is important, as in the storage or processing of food or beverages. Here, in order to be safe, the cleaning process has to be greatly extended so as to guarantee absolute cleanliness.

A method is furthermore known which attempts to determine whether the metal surface is freed from contamination during the cleaning process via the contribution of this exposed metal surface to the conductivity of an electrolytic system. Thus, according to "Deutsche Textiltechnik" 10 (1960), pp. 589–593, a standardized fatty contamination is applied to two platinum wires and the decline in surface coverage is traced by the discontinuous measurement of the electrolytic conductivity between two platinum wires, the resistance being measured with a Wheatstone bridge. It is mentioned that the desired ideal arrangement for this method is an "autographic measuring bridge". Because of the limitation to liquids with badly conducting anionic, or even non-ionogenic detergents, it is necessary to add an electrolyte, because of which the cleaning result may be influenced (e.g. in the case of cleaning agents containing polyphosphate). No mention is made of an extension of the process to other metals than platinum, such as the stainless steel or aluminum customarily used in container, instrument and pipe designs.

There was therefore a need for a process to control the cleanliness of metallic surfaces, which is not afflicted with the above-mentioned disadvantages and which, above all, can be used quickly, continuously, reliably and universally for different metals and a plurality of cleaning agents and cleaning processes for the most varied contaminations.

SUMMARY OF THE INVENTION

Pursuant to the invention it has been possible to solve the foregoing problem in keeping with the demand and the above-described difficulties by means of a process for the control of the cleaning procedure of metallic interior walls of vessels or pipes through flooding, or turbulent impacting with highly alkaline or highly acid cleaning liquids.

The process for cleaning the interior wall of a metal vessel or pipe comprises flooding or turbulently impacting the interior wall of said vessel or pipe with a strongly alkaline or strongly acidic cleaning fluid, simultaneously measuring the conductivity of the cleaning fluid between two electrodes located in the interior of said vessel or pipe and terminating said flooding or impacting when the measured conductivity has been substantially restored to the level measurable with clean electrodes. There is also disclosed an apparatus for performing the process.

The process is performed with an apparatus comprising a metal vessel or pipe having in the interior two electrodes which are electrically insulated with respect to each other, means for flooding or turbulently impacting the interior walls of said metal vessel or pipe with a strongly alkaline or strongly acidic cleaning fluid, and conductivity measuring means conductively connected to said electrodes.

DETAILED DESCRIPTION OF THE PREFERRED EMBODIMENTS

Figure 2:
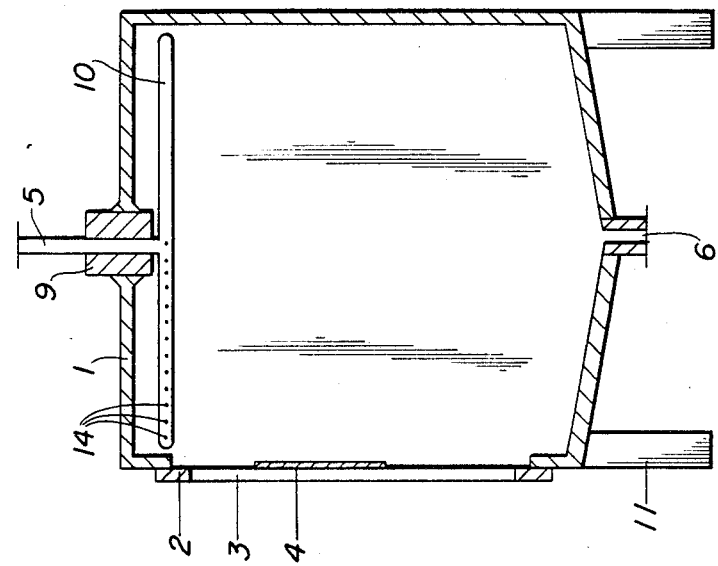

Preferably, the process of the present invention is carried out in such a way that the cleaning procedure is maintained until at least 90, 95, or even 99% of the conductivity is reached, which is measurable with uncontaminated electrodes. The ultimate conductivity to be reached depends mainly upon the purpose for which the container, pipe or apparatus is to be used. For example, in foodstuff processing the goal would be conductivity values of about 99% of the conductivity value with uncontaminated electrodes.

Preferably, the conductivity values of the cleaning liquids measured in the process pursuant to the invention are in a range between 5 and 200 mS·cm$^{-1}$, more preferably in a range between 5 and 100 mS·cm$^{-1}$, and most preferably in a range between 5 and 80 mS·cm$^{-1}$. Cleaning liquids customarily used in the food industry have conductivity values between 20 and 80 mS·cm$^{-1}$.

The cleaning liquids to be used in the process pursuant to the invention could e.g. be made up of the following basic components; inorganic substances (lyes, acids, salts) as main constituents, sequestering agents, and detergents.

Preferably, the temperature of the cleaning liquid lies within the range of the operating temperatures, i.e. the temperature to be maintained when using the vessels or pipes for the intended purpose. Preference is given to cleaning liquid temperatures above the temperature at which the contamination melts.

The process pursuant to the invention is carried out with an apparatus which comprises a flooding or impacting device for the cleaning liquid in the container or pipe, and which is characterized by the fact that the vessel or pipe wall consists of two parts, electrically insulated with respect to each other, which, as electrodes, are conductively connected with a conductivity measuring device.

Preferably, the process pursuant to the invention is carried out with an apparatus in which a metal plate is embedded in the wall of the container or pipe in an insulated fashion, whereby, in each case, the metal plate is the one, and the container or pipe wall is the other electrode. A synthetic resin may be used to embed the metal plate in the wall. With a view to the electrochemical contact potential series, the material of the two metal electrodes of the device pursuant to the invention may be the same, or different. Preferably, use is made of electrodes of the same material. When different electrode materials are used, preference is given to metals with a potential difference of at most 10 mV.

In the same manner, the two metal electrodes may be the same, or different, with respect to their surface roughness. In case of a difference in surface roughness, the smaller electrode may have a greater, as well as a lesser, roughness depth than the larger electrode. That will depend upon whether the dirt particles in question adhere better at a greater, or a lesser, roughness depth. In order to be representative of the cleanliness control, it is preferable for the smaller electrode to have such a nature, that the dirt particles adhere more strongly to it, than to the larger electrode (container or pipe wall).

The size ratio of the surface of the two electrodes has practically no influence on the accuracy of the conductivity measurement. The cleanliness control is the more representative, the larger the area of the measuring electrode. Of course, the accuracy of the measurement declines with an increasing area of the measuring electrode. The area of the measuring electrode should be at least equal to, or larger than, the dirt particles to be detached. This applies in particular when the cleaning process does not consist of a uniform detaching or de-emulsifying of the contamination, but of a preceding undermining of these contaminations by the cleaning liquid, followed by detaching from the wall of dirt particles, by means of mechanical influences. Preferably, the area of the smaller electrode should be larger than the average area of the dirt particles detaching in such a way. It is especially preferred that the area of the smaller electrode is between 5 and 50 times larger than the average area of the detaching dirt particles.

It is advantageous for the measuring electrode to be located at the place of greatest contamination of the container or pipe. The place of the greatest contamination may e.g. be the bottom of the container, or the border region between liquid and gas space above it, or between two immiscible liquids.

In case of a turbulent impacting of the container or pipe with the cleaning liquid, the strength and unformity of the flushing layer are not critical. Fluctuations in conductivity occurring due to the operating rhythm of the impacting device can to a great extent be attenuated in a known manner by a compensator in the measuring circuit, so that the measuring indication can be stabilized.

The inventive cleanliness control process, by a measurement of the electrical conductivity, is distinguished by the fact that it can be used continuously, rapidly and universally for different container and pipe materials, the most varied contaminations, and with a large number of cleaning liquids.

The process of the present invention is not only suitable for the determination of the end point of a cleaning process, which has been reached when the conductivity value is measured, that has been obtained with the clean electrodes. Rather, it is also possible to trace the entire cleaning process by means of measurements, so that, based on the resulting conductivity curves, peculiarities of the cleaning process, of the cleaning liquids used, or of the contaminations can be indicated. Thus, one can e.g. quickly determine the serviceability of various washing agents, which is of particular interest in connection with compounding of new washing agents, for new applications of known washing agents, or for a demonstration of the conductivity of cleaning agents to customers.

In general, in a cleaning process leading to a complete removal of the contaminations, one reaches a conductivity value of maximally 99% referred to the conductivity of the impure solution, measured with absolutely clean electrodes, at the end of the process. The conductivity value of the clean electrode should be determined with a cleaning liquid containing as much as possible the same quantity of impurities, and at the same temperature, which are generally present in the cleaning liquid after termination of the intended cleaning process. It will hardly be possible to exceed a value of 99%, because, in normal cleaning processes, the last impurities are strongly adsorbed by the surface.

When measuring electrodes for a control of the cleaning liquid have already been installed, the cleaning procecure is continued for such a length of time, until the conductivity value measured with the measuring electrodes corresponds to an established value which represents that measurable with clean electrodes.

A peculiarity during a cleaning process, which can be determined by means of the process pursuant to the invention is e.g. the effect of a recontamination due to the chemical conversion of already removed contamination products and their reattachment to the electrodes. The process pursuant to the invention can also be used to trace the flushing process for the removal of the cleaning liquid, which follows the cleaning process (decline in conductivity).

Due to these advantages, the process for a cleanliness control pursuant to the invention is especially well suited for applications in the field of beverages and food, in which highest demands are made of cleanliness. Here, use is generally made of strongly alkaline and acidic cleaning liquids.

Figure 1:
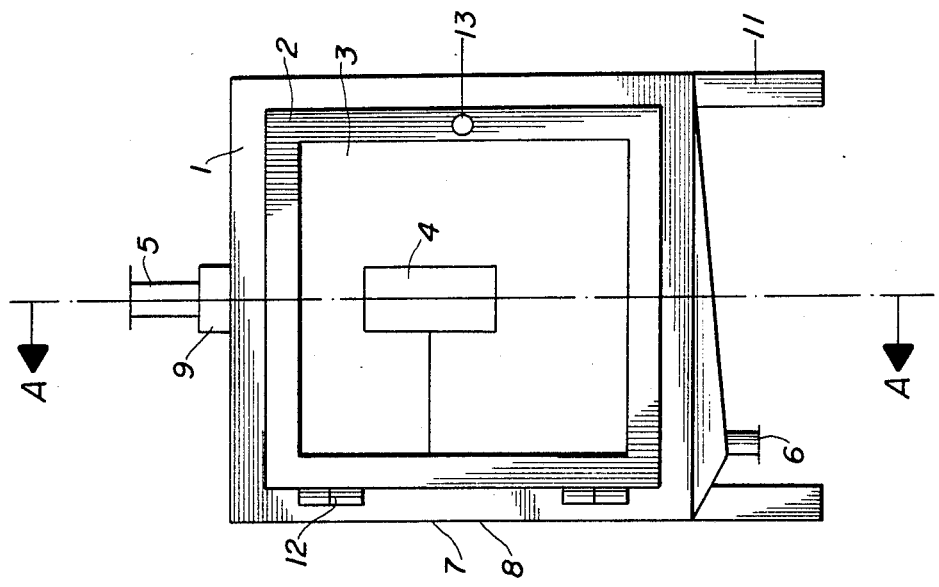

The invention is explained in greater detail on hand of the following experimental nonlimiting examples and illustrations. The following is shown:

FIG. 1: Front view of an experimental tank.

FIG. 2: Section AA through the experimental tank of FIG. 1.

EXAMPLE 1

In order to be able to trace the removing of contaminations of various origins from tank walls, use was made of an experimental tank 1 pursuant to FIGS. 1 and 2. In its front, experimental tank 1, mounted on legs 11, has a door 2, which is connected to experimental tank 1 via higes 12 and is lockable via door fastening handle 13. A viewing glass 3 is mounted in door 2, permitting observation of the interior of the tank. An electrode 4 is pasted on the inside of the pane of glass 3, which electrode, like experimental tank 1 and door 2, is made of stainless steel. The surface condition of electrode 4 and of the interior walls of experimental tank 1 is likewise identical. Experimental tank 1, on the one hand, and electrode 4, on the other hand, are connected to a conductivity measuring device via electrically conductive cables 7, or 8.

The interior walls of the tank, and the inside of the door, are impacted in surges through means that are as such known. Thereby, the cleaning liquid is supplied to a revolving spray pipe 10 via cleaning liquid supply pipe 5. Spray pipe 10 has outlet holes 14, directed laterally upward, through which the cleaning liquid is sprayed into the interior of the tank. The cleaning liquid is conducted to the supply pipe 5 via a not shown pump and a likewise not shown line, while spray pipe 10 is revolved around the axis of supply pipe 5, supply pipe 5 and spray pipe 10 being revolvably mounted on a bearing 9. The cleaning liquid is collected in the bottom of experimental tank 1 and removed via discharge pipe 6. To carry out the cleaning of the walls contaminated with hop resin, use was made of a cleaning liquid of: inhibited phosphoric acid, phosphonic acid, detergents and antifoam agent as stable mixture in water at concentrations of 1% (corresponding to 7 mS·cm$^{-1}$) to 3% (corresponding to 21 mS·cm$^{-1}$).

First, the still clean electrode 4 was glued to glass pane 4 of experimental tank 1 with a synthetic resin. The tank walls, as well as electrode 4 consisted of stainless steel. The tank walls and electrode 4 had the same roughness depth. A conductivity of 7 mS·cm$^{-1}$ was found during turbulent impacting with the above-mentioned 1% cleaning liquid. This measured conductivity value was recorded as the value of the uncontaminated electrode.

Now, electrode 4, which was 10 cm long, 5 cm wide and 1 mm thick, and which had again been removed from the experimental tank, was coated with hop resin extract in the following manner:

Dilution of the hop resin extract with methanol at a ratio of 1:1;
application of the dilution to electrode 4 with a brush;
drying of the application for one day at room temperature.

After electrode 4 had again been pasted to glass pane 3, the tank walls and the soiled electrode 4 were subjected to turbulent impacting with the cleaning liquid. The conductivity value measured at the start of cleaning was practically 0 mS·cm$^{-1}$ and rose continuously within an hour to about 6.9 mS·cm$^{-1}$, whereupon the cleaning procedure was terminated. Afterwards, the electrode had the original, bright appearance.

Subsequently, the tank walls and electrode 4 were rinsed with water, until the conductivity value had dropped to 0 mS·cm$^{-1}$. This experiment shows clearly, that, using the process on which the invention is based, it is possible to check the progress of cleaning, the cleaning result, and the rinsing procedure which follows, in an advantageous and particularly in an economical manner.

EXAMPLE 2

In the cleaning of beer barrels, use is as a rule made of a spraying head with nozzle insert, which is introduced into the barrel from below. With the spraying head introduced into the barrel, the inside of the barrel wall can be hit everywhere by the cleaning liquid, which can then flow out downward, together with the detached contamination. The beer barrels are preponderantly made of aluminum.

To clean the aluminum beer barrel, use is now made of a stainless steel spraying head mounted at the end of an electrically non-conducting polyethylene pipe as the one, and of the aluminum barrel as the other electrode. The spraying head is connected to the conductivity measuring instrument by means of an electrically conductive wire. The barrel is placed on electrically conductive contacts, which are likewise conductively connected to the conductivity measuring instrument.

In order to determine the conductivity value of the clean electrode, the spraying head is introduced into a clean barrel and the walls are sprayed with the cleaning liquid at the temperature customarily used for cleaning.

The conductivity value is now measured during cleaning of a soiled beer barrel and the cleaning procedure is continued until the conductivity value of the clean electrode has almost been reached.

This kind of cleaning procedure can be especially favorably applied to automatic barrel cleaning machines with several cleaning and rinsing stations, whereby the conductivity values are in each case measured at the last cleaning and the last rinsing station. The barrels are moved on, when both predetermined conductivity values have been reached.

What is claimed is:

1. An apparatus comprising a metal vessel or pipe having exposed to the interior thereof two electrodes which are electrically insulated and separated from each other, at least one of said electrodes being exposed to contamination in said vessel or pipe, and wherein one of said electrodes comprises an inner wall of said vessel or pipe, means for flooding or turbulently impacting the interior walls of said metal vessel or pipe with a strongly alkaline or strongly acidic cleaning fluid, and conductivity measuring means conductively connected to said electrodes.

2. The apparatus of claim 1, wherein a metal plate is embedded in an insulated manner in a wall of the vessel or pipe, whereby the metal plate is the other said electrode.

3. The apparatus of claim 1, wherein said electrodes are composed of such materials that there exists a potential difference of at most 10 mV between said electrodes.

4. The apparatus of claim 1, wherein both said electrodes consist of the same material.

5. The apparatus of claim 4, wherein the surface finish of the two electrodes is the same.

6. The apparatus of claim 4, wherein said electrodes comprise a smaller electrode and a larger electrode.

7. The apparatus of claim 6, wherein the surface of the smaller electrode has a greater roughness depth than the surface of the larger electrode.

8. The apparatus of claim 6, wherein the surface of the smaller electrode has a lower roughness depth than the surface of the larger electrode.

9. The apparatus of claim 6, wherein the area of the smaller electrode is larger than the average area of dirt particles to be detached from said vessel or pipe.

10. The apparatus of claim 9, wherein the area of the smaller electrode is between 5 and 50 times larger than the average area of said dirt particles.

11. The apparatus of claim 10, wherein the smaller electrode is located in a region of said vessel or pipe of heaviest contamination by said dirt particles.

12. The apparatus of claim 1, wherein one of said electrodes is a measuring electrode, and said measuring electrode is located in a region of said vessel or pipe of heaviest contamination by dirt particles to be detached from said vessel or pipe.

13. The apparatus of claim 1, wherein the other said electrode is detachable from said vessel or pipe.

14. The apparatus of claim 1, wherein the other said electrode is the flooding or impacting means.

15. The apparatus of claim 14, wherein said flooding or impacting means is detachable from said vessel or pipe.

16. The apparatus of claim 15, wherein said flooding or impacting means is a spraying head.

17. The apparatus of claim 14, wherein said flooding or impacting means is a spraying head.

* * * * *

UNITED STATES PATENT AND TRADEMARK OFFICE
CERTIFICATE OF CORRECTION

PATENT NO. :   4,586,523
DATED      :   May 6, 1986
INVENTOR(S) :  Rudolf JUENGER It is certified that error appears in the above-identified patent and that said Letters Patent is hereby corrected as shown below:

Column 1, line 23, delete "to".

Column 4, line 34, change "procecure" to --procedure--.

Column 4, line 66, change "higes" to --hinges--.

Signed and Sealed this

Fourteenth Day of October, 1986

[SEAL]

Attest:

DONALD J. QUIGG

*Attesting Officer*     *Commissioner of Patents and Trademarks*